US005942009A

United States Patent [19]
Burns

[11] Patent Number: 5,942,009
[45] Date of Patent: Aug. 24, 1999

[54] SAME-DAY WAVING AND COLORING OF HAIR

[75] Inventor: Michael S. Burns, Doylestown, Pa.

[73] Assignee: BRG, Ltd., Newtown, Pa.

[21] Appl. No.: 08/822,928

[22] Filed: Mar. 28, 1997

[51] Int. Cl.[6] .................................. A45D 7/04; A61K 7/13
[52] U.S. Cl. ................... 8/432; 8/406; 8/563; 8/587; 8/618; 8/625; 8/629; 8/930; 132/204; 132/205; 132/208; 132/209
[58] Field of Search ................... 8/406, 431, 432, 8/563, 618, 625, 629, 930, 587; 132/204, 205, 206, 208, 209; 424/70.4, 70.5, 70.51

[56] References Cited

U.S. PATENT DOCUMENTS

| | | | |
|---|---|---|---|
| 2,540,494 | 2/1951 | Schwartz | 132/205 |
| 2,719,104 | 9/1955 | Westerberg | 8/432 |
| 2,776,668 | 1/1957 | Morgan | 8/432 |
| 3,215,605 | 11/1965 | Soloway | 8/425 |
| 3,266,994 | 8/1966 | Reiss et al. | 8/127.51 |
| 3,368,941 | 2/1968 | Boosen | 8/416 |
| 3,396,736 | 8/1968 | Shansky | 132/208 |
| 3,399,682 | 9/1968 | Isaji | 132/204 |
| 3,399,683 | 9/1968 | Forbiger et al. | 132/205 |
| 3,415,606 | 12/1968 | Randebrock | 8/432 |
| 3,567,355 | 3/1971 | Boosen et al. | 8/432 |
| 3,865,930 | 2/1975 | Abegg et al. | 424/70.4 |
| 3,912,446 | 10/1975 | Zviak et al. | 8/425 |
| 3,957,065 | 5/1976 | Busch et al. | 132/204 |
| 3,966,397 | 6/1976 | Leon et al. | 8/432 |
| 3,993,436 | 11/1976 | Fujinuma | 8/432 |
| 4,149,848 | 4/1979 | Bugaut et al. | 8/410 |
| 4,173,453 | 11/1979 | Shiah | 8/405 |
| 4,186,188 | 1/1980 | Gumprecht et al. | 424/70.14 |
| 4,494,557 | 1/1985 | Nagel | 132/204 |
| 4,566,875 | 1/1986 | Grollier et al. | 8/406 |
| 4,630,621 | 12/1986 | Pontani | 132/204 |
| 4,658,839 | 4/1987 | Dallal et al. | 132/203 |
| 4,776,856 | 10/1988 | Tennigkeit et al. | 8/406 |
| 4,793,992 | 12/1988 | Mathews et al. | 424/538 |
| 4,840,791 | 6/1989 | Mathews et al. | 132/202 |
| 4,906,461 | 3/1990 | Chambers | 424/74 |
| 4,947,878 | 8/1990 | Crews et al. | 132/203 |
| 4,992,077 | 2/1991 | Tennigkeit et al. | 8/406 |
| 5,006,127 | 4/1991 | Tennigkeit et al. | 8/406 |
| 5,015,470 | 5/1991 | Gibson | 514/2 |
| 5,034,226 | 7/1991 | Beck | 424/195.1 |
| 5,051,252 | 9/1991 | Schultz et al. | 132/204 |
| 5,094,662 | 3/1992 | Schultz et al. | 8/406 |
| 5,101,841 | 4/1992 | Crews et al. | 132/203 |
| 5,139,772 | 8/1992 | Morita et al. | 424/70.1 |
| 5,161,553 | 11/1992 | Cohen et al. | 132/205 |
| 5,188,639 | 2/1993 | Schultz et al. | 8/406 |
| 5,241,973 | 9/1993 | Salce et al. | 132/205 |
| 5,338,540 | 8/1994 | Lee et al. | 424/70.4 |
| 5,340,367 | 8/1994 | Schultz et al. | 8/432 |
| 5,635,168 | 6/1997 | Burns et al. | 424/70.4 |
| 5,681,554 | 10/1997 | Cannell et al. | 424/70.14 |
| 5,715,845 | 2/1998 | Samain | 132/204 |

FOREIGN PATENT DOCUMENTS

| | | |
|---|---|---|
| 0 083 095 | 7/1983 | European Pat. Off. . |
| 0 328 816 | 2/1988 | European Pat. Off. . |
| 0 260 716 | 3/1988 | European Pat. Off. . |
| 0 352 375 | 1/1990 | European Pat. Off. . |
| 0 443 356 | 7/1993 | European Pat. Off. . |
| 2 028 818 | 12/1970 | Germany . |
| 4 211 451 | 10/1993 | Germany . |
| 4 331 136 | 8/1994 | Germany . |
| 53-96336 | 8/1978 | Japan . |
| 60-100512 | 6/1985 | Japan . |
| 1-066109 | 3/1989 | Japan . |
| 2153865 | 8/1985 | United Kingdom . |
| WO 96/09030 | 3/1996 | WIPO . |

OTHER PUBLICATIONS

Redken advertisement, "CAT–TM–Protein Network System," p. 1, 1990 (no month available).
English language translation of JP 64–66,109, Sanshido Seiyaku, pp. 1–53, Mar. 1989.
Croda Inc., Product List, pp. 1, 7, 8 (Apr. 1990).
Croda Inc., HYDROTRITICUM 2000 Data Sheet, 2 pages (May 2, 1994).
Croda Inc., HYDROSOY 2000/SF Data Sheet, 2 pages (Jul. 19, 1984).
Croda Inc., CROQUAT WKP Data Sheet, 5 pages (1988). No month available.
Croda Inc., CROTEIN WKP Data Sheet, 4 pages (Nov. 13, 1981).
Prodesign International, "Pro–Ionic Quench—Perm Rinse Eliminator," 3 pages (1993/1994). No month available.
*Hawley's Condensed Chemical Dictionary*, entries for "cysteine," "cystine," and "keratin" (11th ed. 1987). No month available.
M.S. Balsam (editor), *Cosmetics Science And Technology*, vol. 2, pp. 224–229 (second edition 1972). No month available.
W.A. Poucher (revised by G.M. Howard), *Perfumes Cosmetics and Soaps*, vol. 3, pp. 93–105 (eighth edition 1974). No month available.
*The Merck Index*, p. 2773, entry for "cystine" (10th ed. 1983). No month available.

*Primary Examiner*—Caroline D. Liott
*Attorney, Agent, or Firm*—Bryan Cave LLP

[57] ABSTRACT

A method for the same-day permanent waving and coloring of hair ("same-day" meaning during a twenty-four hour period and preferably during a single session of only a few hours), which can provide to the hair improved shape retention, color receptivity, color stability, color retention, color evenness, color depth, shine, strength, softness, luster, and/or elasticity. After initial preparation (shampooing, treating with a pre-wrap, and placing on rods if the hair is to be curled), the hair is processed using a waving agent (e.g., thioglycolate), the excess is preferably removed, contacted with a first composition, the excess preferably removed, optionally but preferably contacted with a second composition, heated to dry the hair, and then contacted with a coloring composition containing an oxidative colorant and an oxidizing agent, the oxidizing agent helping develop the color and rebond the hair. The first and second compositions each contain a biologically acceptable metal (preferably a polyvalent metal, e.g., magnesium) and optionally a proteinaceous material (preferably containing cystine).

42 Claims, No Drawings

SAME-DAY WAVING AND COLORING OF HAIR

BACKGROUND OF THE INVENTION

The invention concerns hair treating compositions and their methods of use and, more specifically, compositions and methods for the same-day waving (also known as "permanent waving" or "perming") and coloring (also known as "dyeing" or "tinting") of hair.

Hair treating compositions and methods for treating hair have been used for many years. Compositions used include coating compositions to hold hair in a particular manner and compositions to improve hair strength, shine, color, arrangement, or other properties or to prevent or repair damage to hair. Current popular hair treatments include permanent waving and hair coloring, both of which involve chemical treatments that tend to damage hair.

There are numerous methods and compositions for permanent waving, which involves arranging the hair in the desired configuration and then treating the hair to semi-permanently retain the arrangement. (As used herein, the term "waving" should be understood to include both curling and straightening.) The initial step is a waving step in which the hair is "relaxed" by breaking the disulfide bonds in the keratin of the hair using a reducing agent. Compositions used to break those bonds include solutions of thioglycolic acid (at pH 8.5–9.5 if an alkaline wave or pH 6.5–6.95 if an acid wave) or a sulfite/bisulfite solution (at pH 5.5–8.5) containing alkalis such as alkali metal compounds, ammonium hydroxide, or amines (e.g., monoethanolamine) to provide the alkaline pH. After reducing or breaking the keratin's disulfide bonds, the hair is fixed in the desired arrangement using an oxidizing agent (e.g., hydrogen peroxide or sodium bromate) to reestablish disulfide bonds in the keratin.

The reduction within the hair fiber is of the amino acid cystine, which contains a centrally located disulfide bond. When this bond in a cystine molecule is cleaved using the reducing solution (usually called the "waving solution"), the cystine molecule forms two molecules of the amino acid cysteine, each having a terminal sulfhydryl group resulting from the disulfide cleavage.

If the hair is to be curled, the hair is typically rolled onto rods of various sizes, contacted with the reducing (or waving) solution, and permitted to remain in contact with the solution until the required amount of reduction has occurred. Typically, the at-least-partially-spent reducing solution or lotion is thoroughly rinsed from the hair, the hair is towel dried, and the neutralizer (oxidizing composition) is applied. The neutralizer reoxidizes the sulfhydryl groups to disulfide groups to fix the hair in the new arrangement. If curls are required, the hair is neutralized while still on the rods. Hair may also be straightened, i.e., the natural curl removed from the hair, in which case the hair is combed while in contact with the reducing solution and then combed while the neutralizer or oxidizing solution is applied. In either case (curling or straightening), the procedure is completed by rinsing the neutralizer (oxidizer) from the hair. It is usually recommended that hair not be shampooed for at least 24 hours after the permanent waving procedure to provide the tightest curl or straightest hair, as the case may be, because even after removal of the oxidizing solution from the surface of the hair, reaction within the hair (i.e., reformation of disulfide bonds) continues.

The typical waving process requires a rinsing step between the application of the reducing solution and the application of the oxidizing (neutralizing) solution. This intermediate rinse is widely thought to be needed to remove as much of the reducing solution as possible from the hair because the pH of the reducing solution is usually higher than that of the oxidizing solution and if left on the hair in any significant amount, the reducing solution would react with a significant amount of the oxidizing (neutralizing) solution and reduce the latter's effectiveness, especially in the hair fibers into which the oxidizing solution had poorly penetrated. The failure to reform enough disulfide bonds, e.g., if the neutralizer were not sufficiently effective (as would be the case if the reducing solution left on the hair significantly reduced the efficacy of the neutralizer), is highly undesirable because the resulting hair will have poor curl and tend to be straw-like, brittle, feel rough, etc. Hence, the generally recognized need for the intermediate rinse.

On the other hand, it would be desirable to eliminate the intermediate rinse, that is, to use a "rinse-free waving process," because the rinsing step: causes loss of keratin, amino acids, and color from the hair fiber; causes physical damage to the cuticle and cortex of the hair because of the pressurized water jets typically used in hair salons during rinsing; utilizes approximately nine gallons of water with every permanent; is time-consuming, thereby reducing the number of permanent wave customers a hair salon can service per day; and causes swelling of the fiber over and above that caused by the waving lotion. The damage caused by excessive swelling is generally irreversible.

A product marketed under the name PRO-IONIC QUENCH™ from Pro-Design International is said to be useful in a rinse-free waving process in which two different solutions are applied to the hair after waving and blotting and before neutralization. The first solution is believed to have a pH of about 8.3, to contain a bicarbonate salt, and to have only about 5 parts per million of magnesium. The second solution is believed to have a pH of about 2.4 and to contain about 4.5% magnesium sulfate, some citric acid or sodium citrate, and some HYDROTRITICUM (which contains about 1.8% cystine).

It is known that the best time to place hair strengthening agents into the cortex of the hair is after the waving solution has swollen the fiber, which swelling opens the cortex, and before the neutralizer deswells or shrinks the fiber. It is also known that it is desirable to protect the cuticle and cortex of the hair from the damaging effects of the neutralizer solution.

There are many different methods and compositions for coloring hair. Some methods merely apply the colorant to the outside of the hair, but in such cases the colorant can usually be easily removed (e.g., washed out) from the hair. Many different kinds of dyes that penetrate the hair and that are said to react in the hair and/or with the constituents of the hair have also been used. One class of colorants are the oxidative dyes, which are generally applied to the hair along with a developer or oxidizing agent (typically hydrogen peroxide).

There have been a number of attempts to provide compositions and processes that would allow same-day waving and coloring of hair (by "same-day" is meant waving and coloring processing of the hair occurring within a single twenty-four hour period and preferably during one session, a session typically lasting not more than about six hours). See, e.g., U.S. patent application Ser. No. 08/310,270, filed Sep. 24, 1994, now U.S. Pat. No. 5,635,168, by Michael S. Burns (the present inventor) and Herbert E. Edelstein, and PCT Patent Application No. PCT/US95/11649, published under Publication No. WO 96/09030 on Mar. 28, 1996, which corresponds thereto; U.S. Pat. Nos. 3,368,941; 3,396,736; 3,399,682; 4,630,621; 4,776,856; 4,992,077; 5,006,127; 5,094,662; 5,161,553; 5,188,639; 5,340,367; EP 0 260 716; EP 0 328 816; EP 0 352 375; JP Kokai No. 96336-1978; and W. A. Poucher (revised by G. M. Howard), *Perfumes, Cosmetics and Soaps*, volume 3, pages 93–105 (8th edition 1974). (All of the documents listed or otherwise identified or referenced anywhere in this document are hereby incorporated in their entireties for all purposes.)

The following documents also concern hair and the components thereof, hair treatment methods, and hair treatment compositions: U.S. Pat. Nos. 2,540,494; 2,719,104; 2,776,668; 3,215,605; 3,266,994; 3,399,683; 3,415,606; 3,567,355; 3,865,930; 3,912,446; 3,957,065; 3,966,397; 4,149,848; 4,173,453; 4,186,188; 4,494,557; 4,566,875; 4,658,839; 4,793,992; 4,840,791; 4,906,461; 4,947,878; 5,015,470; 5,034,226; 5,051,252; 5,101,841; 5,139,772; 5,241,973; 5,338,540; EP 0 083 095; EP 0 443 356; DE 2 028 818; DE 4 211 451; DE 4 331 136; U.K. 2,153,865; Japan 60-100512; Croda Inc., Product List, pages 1, 7, 8 (April 1990); Croda Inc., HYDROTRITICUM 2000 Data Sheet, 2 pages (May 2, 1994); Croda Inc., HYDROSOY 2000/SF Data Sheet, 2 pages (Jul. 19, 1984); Croda Inc., CROQUAT WKP Data Sheet, 5 pages (1988); Croda Inc., CROTEIN WKP Data Sheet, 4 pages (Nov. 13, 1981); Prodesign International, "PRO-IONIC QUENCH—PERM RINSE ELIMINATOR," 3 pages (1993/1994); *Hawley's Condensed Chemical Dictionary*, entries for "cysteine," "cystine," and "keratin" (11th ed. 1987); M. S. Balsam (editor), *Cosmetics Science And Technology*, volume 2, pages 224–229 (second edition 1972); *The Merck Index*, p. 2773, entry for "cystine" (10th ed. 1983); and Redken advertisement, "CAT™ Protein Network System," 1 page (1990).

Some of the same-day combined processes have attempted to make use of the fact that hydrogen peroxide is typically used as the neutralizer in hair waving processes and is also typically used as the developer for oxidative dyeing of the hair. See, e.g., U.S. Pat. No. 4,630,621. The art has also taught that oxidative dyestuffs cannot be successfully employed with permanent waving compositions in a simultaneous waving/coloring process (see, e.g., U.S. Pat. No. 5,188,639 at column 3, lines 5–13).

In addition to the efforts to develop satisfactory same-day waving and coloring processes, both the waving and coloring steps of which involve chemical treatments that tend to damage hair, many attempts have been made to develop compositions that prevent or repair hair damage arising from various causes. See, e.g., U.S. Pat. Nos. 3,266,994; 4,186,188; 4,494,557; 4,658,839; 4,793,992; 4,906,461; 5,015,470; 5,051,252; U.K. 2,153,865; and EP 0 443 356.

Some hair treating compositions include salts (e.g., salts of polyvalent metals); see, e.g., U.S. Pat. Nos. 3,266,994; 5,051,252; and U.K. 2,153,865. Some hair treating compositions include proteins or polypeptides or amino acids (e.g., keratin, which is an important constituent of hair, nails, wool, and feathers, or low molecular weight protein fragments such as hydrolyzed protein, or amino acids such as cystine and cysteine, the first of which is a constituent of the keratin in the hair and the second of which results from the cleavage of cystine); see, e.g., U.S. Pat. Nos. 4,186,188; 4,494,557; 4,658,839; 4,793,992; and EP 0 443 356. Some hair treating compositions use proteinaceous material and salt. See, e.g., U.S. Pat. No. 4,494,557. Some hair treating compositions include acids (e.g., mineral acids or carboxylic acids such as citric acid); see, e.g., U.S. Pat. Nos. 3,266,994; 4,793,992; 4,906,461; and 5,015,470. Some hair treating compositions use all three types of materials, namely, salts of polyvalent metals, proteins or polypeptides or amino acids, and mineral or carboxylic acids; see, e.g., U.S. Pat. Nos. 4,793,992 and 4,906,461.

Proteins said to be useful in hair treatment by their purveyor, Croda Inc., include HYDROTRITICUM 2000 (hydrolyzed whole wheat protein, which has an average molecular weight of 3,000, is available as a 20% solution, contains 1.8% cystine, and is said typically to be used at a 1–5% level) and other HYDROTRITICUM preparations, HYDROSOY 2000/SF (hydrolyzed soy protein solution, which has an average molecular weight of about 4,000, is available as a 20% solution, contains 1.0% cystine, and is said typically to be used at a 0.2–3% level), KERASOL (a soluble keratin preparation, which has an average molecular weight of about 125,000), CROQUAT WKP (hydrolyzed animal-based keratin, which has an average molecular weight of about 1,000, is available as a 30% solution, contains about 10.2% cystine, and is said typically to be used at a 0.25–2% level) and other CROQUAT preparations, CROTEIN WKP (hydrolyzed animal-based [wool-based] protein, which has an average molecular weight of about 600, is available as a 22% solution, contains about 10.2% cystine, and is said typically to be used at a 0.2–3% level) and other CROTEIN preparations, and CROSILQUAT (cocodimonium silk amino acids, which has an average molecular weight of 320, is available as a 30% solution, contains 0.2% methionine, and contains 0.1% cystine). The presence of cystine in some of these materials is said by Croda to be particularly desirable because, among other reasons, the cystine can permanently bind to the hair under certain conditions and can minimize the loss of cystine from the keratin of the hair during waving.

Despite the many attempts to satisfy the long-standing demand for a same-day waving/coloring process, the need remains for such a process that does not unacceptably damage the hair and that allows the waving and coloring to be conducted during a single twenty-four hour period and preferably during a single visit to the hair salon (which typically lasts not more than about six hours). It would also be desirable if the same-day process were rinse-free (i.e., if rinsing between application of the waving/reducing agent and development of the color were not needed) so as to reduce the total number of rinses needed and avoid the harmful effects of rinsing. It would also be desirable if the process imparted improved shape retention, color receptivity, color stability, color retention, color evenness, color depth, shine, strength, softness, luster, and elasticity to the hair.

SUMMARY OF THE INVENTION

A combined waving/coloring process that meets those needs and provide those and additional benefits has now been developed. Broadly speaking, the combined process for waving and coloring hair in the same day (preferably in only a few hours), which can provide to the hair improved shape retention (whether of curled or straightened hair), color receptivity, color stability, color retention, color evenness, color depth, shine, strength, softness, luster, and/or elasticity, comprises the steps:

(a) optionally shampooing the hair;

(b) contacting the hair with a reducing agent to reduce the disulfide bonds in the hair;

(c) optionally removing excess reducing agent from the hair;

(d) contacting the hair with a first composition containing:

(i) one or more first biologically acceptable metals; and
(ii) optionally one or more first proteinaceous materials;
(e) optionally removing excess first composition from the hair;
(f) optionally contacting the hair with a second composition containing:
(i) one or more second biologically acceptable metals; and
(ii) optionally one or more second proteinaceous materials;
(g) drying the hair while at least some of the first composition and/or optional second composition is still in contact with the hair so that substantially all of the hair is substantially dry;
(h) contacting the substantially dry hair with an oxidative coloring agent and an oxidizing agent to color the hair and reform the disulfide bonds in the hair;
(i) optionally contacting the hair with additional oxidizing agent; and
(j) optionally shampooing the hair.

In another aspect, the combined waving and coloring process comprises the steps:
(a) optionally shampooing the hair;
(b) placing the hair on one or more forming members;
(c) contacting the hair while it is on the one or more forming members with a reducing agent to reduce the disulfide bonds in the hair;
(d) optionally removing excess reducing agent from the hair;
(e) contacting the hair while it is on the one or more forming members with a first composition having a pH of less than about 7 and containing:
(i) at least 0.05% by weight total of one or more first biologically acceptable metals; and
(ii) at least 0.01% by weight total of one or more first cystine-containing proteinaceous materials that can form disulfide bonds involving the keratin of the hair;
(f) optionally removing excess first composition from the hair while it is on the one or more forming members;
(g) contacting the hair while it is on the one or more forming members with a second composition having a pH of less than about 7 and containing:
(i) at least 0.05% by weight total of one or more second biologically acceptable metals; and
(ii) at least 0.01% by weight total of one or more second cystine-containing proteinaceous materials that can form disulfide bonds involving the keratin of the hair;
(h) drying the hair while it is on the one or more forming members and while at least some of the first composition and/or second composition is still in contact with the hair so that substantially all of the hair is substantially dry;
(i) contacting the substantially dry hair while it is on the one or more forming members with an oxidative coloring agent and an oxidizing agent to color the hair and reform the disulfide bonds in the hair;
(j) optionally contacting the hair while it is on the one or more forming members with additional oxidizing agent;
(k) removing the hair from the one or more forming members; and
(l) optionally shampooing the hair.

In another aspect, the combined waving and coloring process comprises the steps:
(a) optionally shampooing the hair;
(b) placing the hair on one or more forming members;
(c) contacting the hair while it is on the one or more forming members with a reducing agent to reduce the disulfide bonds in the hair;
(d) optionally removing excess reducing agent from the hair;
(e) contacting the hair while it is on the one or more forming members with a first composition having a pH of from about 1 to about 6 and containing:
(i) at least 0.05% by weight total of one or more first biologically acceptable polyvalent metals selected from the group consisting of alkaline earth metals, zinc, and aluminum; and
(ii) at least 0.01% by weight total of one or more first cystine-containing proteinaceous materials that can form disulfide bonds involving the keratin of the hair, that together have an average molecular weight of about 5,000 or less, and that together have an average cystine content of at least about 1%, the concentration of the cystine in the first composition being at least about 0.005% by weight;
(f) optionally removing excess first composition from the hair while it is on the one or more forming members;
(g) contacting the hair while it is on the one or more forming members with a second composition having a pH of from about 1 to about 6 and containing:
(i) at least 0.05% by weight total of one or more second biologically acceptable polyvalent metals selected from the group consisting of alkaline earth metals, zinc, and aluminum; and
(ii) at least 0.01% by weight total of one or more second cystine-containing proteinaceous materials that can form disulfide bonds involving the keratin of the hair, that together have an average molecular weight of about 5,000 or less, and that together have an average cystine content of at least about 1%, the concentration of the cystine in the first composition being at least about 0.005% by weight;
(h) drying the hair while it is on the one or more forming members and while at least some of the first composition and/or second composition is still in contact with the hair so that substantially all of the hair is substantially dry;
(i) contacting the substantially dry hair while it is on the one or more forming members with an oxidative coloring agent and an oxidizing agent to color the hair and reform the disulfide bonds in the hair;
(j) optionally contacting the hair while it is on the one or more forming members with additional oxidizing agent;
(k) removing the hair from the one or more forming members; and
(l) optionally shampooing the hair.

In another aspect, the combined waving and coloring process comprises the steps:
(a) optionally shampooing the hair;
(b) placing the hair on one or more forming members;
(c) contacting the hair while it is on the one or more forming members with a reducing agent to reduce a portion of the disulfide bonds in the hair, thereby producing reduced hair;

(d) optionally removing excess reducing agent from the reduced hair;

(e) contacting the reduced hair while it is on the one or more forming members with a first composition having a pH of from about 1 to about 6 and containing:
  (i) at least 0.05% by weight total of one or more first biologically acceptable polyvalent metals selected from the group consisting of alkaline earth metals, zinc, and aluminum; and
  (ii) at least 0.01% by weight total of one or more first cystine-containing proteinaceous materials that can form disulfide bonds involving the keratin of the hair, that together have an average molecular weight of about 5,000 or less, and that together have an average cystine content of at least about 1%, the concentration of the cystine in the first composition being at least about 0.01% by weight;

(f) optionally removing excess first composition from the reduced hair while it is on the one or more forming members;

(g) contacting the reduced hair while it is on the one or more forming members with a second composition having a pH of from about 1 to about 6 and containing:
  (i) at least 0.05% by weight total of one or more second biologically acceptable polyvalent metals selected from the group consisting of alkaline earth metals, zinc, and aluminum; and
  (ii) at least 0.01% by weight total of one or more second cystine-containing proteinaceous materials that can form disulfide bonds involving the keratin of the hair, that together have an average molecular weight of about 5,000 or less, and that together have an average cystine content of at least about 1%, the concentration of the cystine in the first composition being at least about 0.01% by weight;

(h) drying the reduced hair while it is on the one or more forming members and while at least some of the first composition and/or second composition is still in contact with the reduced hair so that substantially all of the reduced hair is substantially dry;

(i) contacting the substantially dry reduced hair while it is on the one or more forming members with an oxidative coloring agent and an oxidizing agent to color the hair and reform a substantial portion of the disulfide bonds in the hair that were reduced in step (c);

(j) optionally contacting the hair from step (i) while it is on the one or more forming members with additional oxidizing agent;

(k) removing the hair from the one or more forming members; and (l) optionally shampooing the hair.

In some preferred embodiments, magnesium is used as a metal in one or both of the first and second compositions, and/or the first and second cystine-containing proteinaceous materials each comprise non-ionic and cationic cystine-containing proteinaceous materials, and/or there is no rinsing of the hair from the time the reducing (waving) composition is applied until after the color has been developed in the hair. In a particularly preferred embodiment, there is no rinsing of the hair from the step of contacting the hair with the reducing agent through the step of drying the hair so that the drying step comprises drying the hair while at least some of the reducing agent, first composition, and (optional) second composition are still in contact with the hair so that substantially all of the hair is substantially dry.

The first composition may be thought of as being the waving solution deactivator or "perm deactivator," because one of its functions is to halt most of the action of the waving solution (e.g., thioglycolate). The second composition, which preferably is used, may be thought of as functioning principally to help the coloring process, in other words, as a "color builder." In fact, both compositions perform both of those functions, as well as other functions, to a greater or lesser degree.

As is well-known in the art, there are different "levels" of color, the lower levels (1–6) being the darker colors, higher levels (7–10) being lighter colors, and still higher levels (11 and higher) being ultra-light colors. The second composition of this process, if used, may have different compositions depending on at which color level the coloring portion of the combined process is aiming. In some cases it may be possible to omit the use of any second composition and have the first composition perform all of the functions. However, it usually will be preferable to use both the first and the second composition.

As is well-known in the art, after a permanent waving treatment, the hair usually should not be further processed for at least 24 hours or else there may be significant loss of the wave imparted by the waving treatment and significant reduction in color retention. It is also generally believed not to be possible to color hair immediately after waving it without risking serious damage to the hair as well as skin and scalp irritation.

Surprisingly, the combined process of this invention can be carried out in less than a day (twenty-four hours) and in a single session, which typically lasts less than six hours, desirably less than five hours, preferably less than four hours, and most preferably less than three hours. Also surprising is the fact that the process imparts improved shape retention, color receptivity, color stability, color retention, shine, strength, and/or color evenness to hair and that the hair also has a more lustrous appearance, a softer hand, is stronger, and is more elastic than hair which has not been contacted with the compositions used herein.

The beauty salon patron whose hair is being treated using such a combined process also benefits in other ways. The patron saves time (travel, scheduling, and intermediate styling time) and money because there is no need to wait a week or so between waving and coloring as is typically the case with conventional waving and permanent coloring. Furthermore, conventional waving processes usually cause the color of previously colored hair to fade. Thus, without the combined process of this invention, the patron would typically have to wait a week or so after waving until the faded color could be restored to the desired color by a coloring session. The salon also benefits from this combined process because salon efficiency, and therefore profitability, are increased by the reduction in both scheduling problems and the risk of cancelled appointments. Other advantages and benefits will be apparent to those skilled in the art.

DETAILED DESCRIPTION OF THE INVENTION

The first composition and optional second composition used in the process of this invention each comprise at least one biologically acceptable metal and optionally (but desirably) a proteinaceous material. The first composition and second composition may also each optionally (but desirably) contain an acid. The first composition and second composition are each preferably aqueous compositions and more preferably aqueous solutions.

The biologically acceptable metals may be any metals that allow the benefits of this invention to be achieved. The biologically acceptable metals are preferably polyvalent metals. The polyvalent metals are preferably introduced as polyvalent metal compounds, which are preferably water-soluble salts of the alkaline earth metals, zinc, and aluminum. By "polyvalent" is meant a valence of more than one. By "alkaline earth metal" is meant a metal in Group IIA of the Periodic Table, which Group includes magnesium and calcium. The heavier metals tend to impart color to the hair and are therefore generally less desirable to use although in specific instances they may be useful. Additionally, some metals, including some of the alkaline earth metals, are less desirable for use in the present invention because of their toxicity, cost, or low solubility. Also, some heavier metals may decompose peroxide and are therefore not preferred if peroxide is used as the oxidizing agent. The term "biologically acceptable metal" should be understood to include not just one but also the total of two or more different biologically acceptable metals. Magnesium is most preferred in part because it generally does not cause tonal shifts in color that many other metals may cause.

Preferably the polyvalent metal compounds are sufficiently water-soluble, are non-toxic, are not too expensive, do not impart any undesired color to the hair, and do not significantly interfere with any peroxide composition used. The preferred metals are calcium, magnesium, zinc, and aluminum, of which magnesium is most preferred; however, any metal may be used provided that the advantages of this invention can be achieved.

Preferably the composition contains at least one water-soluble salt of a metal selected from the group consisting of magnesium, calcium, zinc, and aluminum, of which magnesium is most preferred. Water-soluble salts such as calcium chloride, calcium acetate, magnesium chloride, magnesium sulfate, zinc chloride, zinc sulfate, and aluminum sulfate can be used, of which magnesium sulfate is most preferred.

Magnesium sulfate may be used as such or in its common hydrated form, namely, Epsom salt, which has a formula of $MgSO_4 \cdot 7H_2O$. The $MgSO_4$ per se represents about 120.4 mass units out of the total of about 246.5 mass units for the hydrated form, and Mg represents about 24.3 mass units of that. Thus, the $MgSO_4$ is about 49% of the hydrated form (120.4/246.5), Mg is about 20% of the $MgSO_4$ (24.3/120.4), and Mg is about 10% of the hydrated form (24.3/246.5).

Each of the first and second compositions typically contains at least 0.05% by weight (total) of the at least one (i.e., one or more) biologically acceptable metals, usually at least 0.1% by weight (total) of the one or more biologically acceptable metals, more usually from about 0.15% to about 3%, desirably from about 0.2% to about 2.5%, more desirably from about 0.25 to about 2%, and preferably from about 0.3% to about 1.5%. In the first composition, the total concentration of the one or more biologically acceptable metals is preferably about 1.5% when $MgSO_4 \cdot 7H_2O$ is used to supply magnesium as the biologically acceptable metal (the $MgSO_4 \cdot 7H_2O$ concentration would thus be about 15%). In the second composition, the total concentration of the one or more biologically acceptable metals is preferably about 1% for color levels 1–6 when $MgSO_4 \cdot 7H_2O$ is used to supply magnesium as the biologically acceptable metal (the $MgSO_4 \cdot 7H_2O$ concentration would thus be about 10%) and is preferably from about 0.3% to about 0.45% for color levels 7–10 when $MgSO_4 \cdot 7H_2O$ is used to supply magnesium as the biologically acceptable metal (the $MgSO_4 \cdot 7H_2O$ concentration would thus be from about 3% to about 4.5%).

Without wishing to be bound by any theory, it is believed that one of the functions of the metal or metals used in the compositions of this invention is to help reduce the viscosity of the coloring composition that is applied to the hair to help it penetrate the hair. Generally speaking, the currently commercially available paraphenylene diamine oxidative compositions need to have their viscosities reduced to adequately penetrate the hair. Without wishing to be bound by any theory, it is believed that the metal or metals also help to deswell the hair (swelling damages the hair) and to catalyze the coloring action of the coloring composition while allowing "color lift."

The reference to the weight or concentration of the one or more biologically acceptable metals refers to the metals per se and not, for example, to the rest of the compounds in which they may be contained or to any related water of hydration. Thus, when using Epsom salt to provide magnesium, the sulfate moiety and the water of hydration should be ignored in the calculation. For example, if 1 weight unit of magnesium ions is needed to prepare the first or second composition of this invention, about 5 weight units of $MgSO_4$ per se or about 10 weight units of $MgSO_4 \cdot 7H_2O$ may be used.

The term "proteinaceous material" does not include additives (e.g., stabilizers, emulsifiers) or carriers (for example, solvents or vehicles, such as water or alcohols) that may be present in the mixture containing the proteinaceous material. Thus, for example, if the mixture containing the proteinaceous material is a commercially available mixture normally available as a 30% aqueous solution, the "proteinaceous material" would not include the 70% water and the concentration of proteinaceous material in the first and second composition would be calculated based on the contained water-free proteinaceous material rather than on the whole commercially available aqueous solution.

Each proteinaceous material used in the first and second compositions typically has an average molecular weight of 10,000 or less (although much higher averages can be used in some cases) and can form disulfide bonds involving the keratin of the hair. By "average molecular weight" is meant the average molecular weight of the proteinaceous material per se and not including additives (e.g., stabilizers, emulsifiers) or carriers (for example, solvents or vehicles, such as water or alcohols) that may be present in the mixture containing the proteinaceous material. Any proteinaceous materials may be used provided that they meet those requirements and that in combination with the other ingredients the advantages of this invention are achieved. The preferred proteinaceous materials are preferably cystine-containing proteinaceous materials and most preferably cystine-containing keratin proteinaceous materials.

The average molecular weight of the total proteinaceous material in the first composition and in the second composition is usually 10,000 or less, desirably 5,000 or less, preferably 2,000 or less, and more preferably 1,000 or less. The average molecular weight of the total (i.e., all the proteinaceous materials together in either the first composition or the second composition) may be in the range of 300 to 2,000 and more preferably in the range of 400 to 1,000.

It is believed that molecules of a molecular weight of about 2,000 or less can enter the hair significantly more rapidly and to a greater extent than molecules having a molecular weight of more than about 2,000. Thus, if the proteinaceous materials together in the first composition or in the second composition have an average molecular weight of greater than about 2,000, it is preferred that the proteinaceous materials in the composition together contain a significant number of molecules having a molecular weight of about 2,000 or less so that some portion of the total proteinaceous material can enter each individual hair fiber.

For reasons explained below, molecules that are too small may be less desirable for use as components of the sulfur-containing material. Thus, the average molecular weight of the proteinaceous material will typically be at least 50, more usually at least 100, desirably at least 150, more desirably at least 200, most desirably at least 240, preferably at least 250, more preferably at least 300, and most preferably at least 400.

The total concentration of the proteinaceous materials in each of the first composition of this invention and second composition of this invention is usually at least 0.01% by weight, more usually at least 0.05%, desirably at least 0.1%, more desirably at least 0.2%, and preferably at least 0.3%. The total concentration of proteinaceous materials in each of the first and second compositions of this invention will desirably be in the range of about 0.01% to about 5% by weight, more desirably in the range of about 0.05% to about 3% by weight, most desirably in the range of about 0.1% to about 2% by weight, and preferably in the range of about 0.15% to about 1% by weight. The total proteinaceous material concentration employed in each of the first composition and second composition will depend to some extent on the nature of one or more proteinaceous materials used, its or their average molecular weight(s), what other ingredients are used in each of the first and second compositions, and their concentrations.

In the first composition, the total concentration of the one or more proteinaceous materials is preferably about 0.18% (furnished by 0.4% CROTEIN WKP, which is a 22% proteinaceous material aqueous solution, and 0.3% CROQUAT WKP, which is a 30% proteinaceous material aqueous solution). In the second composition, the total concentration of the one or more proteinaceous materials is preferably about 0.78% for color levels 1–6 (furnished by 1.5% CROTEIN WKP at 22% proteinaceous material and 1.5% CROQUAT WKP at 30% proteinaceous material) and is preferably about 0.63% for color levels 7 and higher (furnished by 1.5% CROTEIN WKP at 22% proteinaceous material and 1.5% CROQUAT WKP at 30% proteinaceous material).

By "proteinaceous material" is meant a material that is or comprises one or more proteins, one or more polypeptides, one or more peptides, one or more amino acids, or mixtures thereof; however, as explained below, amino acid molecules per se are generally too small to form the desired cross-links involving the keratin of the hair and therefore it is preferred that each total proteinaceous material used in each of the first composition and second composition not be only amino acids per se.

Peptides are often considered to comprise two up through several linked amino acids. (Strictly speaking, the units of the peptide are amino acid moieties, that is, molecular units derived from and substantially identical to the amino acids per se except, for example, for their terminal linked ends. When a molecule is said to contain amino acids it will be understood by those skilled in the art to contain amino acid moieties. Thus, a cystine-containing proteinaceous material may be said to contain either cystine per se or cystine moieties.) Polypeptides are often considered to comprise several up to many linked amino acid moieties. Proteins are often considered to comprise many up to hundreds, thousands, or even more linked amino acid moieties. As is apparent, there is often no clear cut dividing line between peptides and polypeptides or between polypeptides and proteins. For reasons explained herein, it is desirable that the total proteinaceous material of the first composition and the total proteinaceous material of the second composition not consist entirely of molecules that are too large or too small. The term "proteinaceous material" should be understood to include not just one but also the total of two or more separate proteinaceous materials. The proteinaceous material may be derived from any source and by any method.

Preferably the proteinaceous material is a cystine-containing proteinaceous material and most preferably a cystine-containing keratin proteinaceous material. When a cystine-containing material is used, its cystine content is usually at least about 0.5% by weight, typically at least about 1% by weight, more typically at least about 2% by weight, desirably at least about 3% by weight, more desirably at least about 4% by weight, most desirably at least about 5% by weight, preferably at least about 6% by weight, more preferably at least about 8% by weight, and most preferably at least about 10% by weight. The most preferred commercially available proteinaceous materials, CROTEIN WKP and CROQUAT WKP, are aqueous solutions and the proteinaceous material per se typically contains about 10.2% cystine. The term "cystine-containing proteinaceous material" should be understood to include not just one but also the total of two or more separate cystine-containing proteinaceous materials used in the composition.

When a cystine-containing proteinaceous material is used in either or both of the first composition and second composition, the cystine content in each is usually at least 0.001% by weight (10 ppm), more usually at least 0.005% (50 ppm), desirably at least 0.01% (100 ppm), more desirably at least 0.015% (150 ppm), most desirably at least 0.02% (200 ppm), and, at least for the second composition, preferably at least 0.03% (300 ppm) and most preferably at least 0.05% (500 ppm). The total cystine content in each of the first and second compositions of this invention will desirably be in the range of about 0.001% to about 0.5% by weight (10 ppm to 5000 ppm), more desirably in the range of about 0.005% to about 0.3% by weight (50 ppm to 3000 ppm), most desirably in the range of about 0.01% to about 0.2% by weight (100 ppm to 2000 ppm), and preferably in the range of about 0.015% to about 0.1% by weight (150 ppm to 1000 ppm).

A mixture of cationic and non-ionic cystine-containing proteinaceous materials works well as the proteinaceous material in the first and second compositions of this invention. If such a mixture is used, the weight ratio of cationic to non-ionic proteinaceous materials should be from 4/1 to 1/4 (the ratio is of active ingredient to active ingredient and does not include any carrier, for example, water, or any other additives). The two preferred cystine-containing proteinaceous materials are CROQUAT WKP, which is cocodimonium hydrolyzed animal keratin and is cationic (average molecular weight of about 1,000; sold as a 30% aqueous solution), and CROTEIN WKP, which is hydrolyzed animal (wool-based) protein and is non-ionic (average molecular weight of about 600; sold as a 22% aqueous solution). A weight ratio of 3 weight units of CROQUAT WKP solution to 4 weight units of CROTEIN WKP solution is preferred. Thus, when the solution concentrations are taken into account, the preferred weight ratio of these cationic to non-ionic materials is equal to (3×30%) divided by (4×22%) or slightly more than 1/1.

It is important that at least some of the proteinaceous material be able to form disulfide bonds involving the keratin of the hair. As used herein, the phrase "can form disulfide bonds involving the keratin of the hair" means that the proteinaceous material can bond to the keratin in the hair through, with, or by means of thiol moieties or disulfide bonds, can form disulfide bonds (e.g., cross-links) between different parts of the keratin of the hair (e.g., can form disulfide bonds to cross-link two cysteines in the hair and thereby form a cystine), and/or can form disulfide bonds that otherwise involve the keratin of the hair.

Amino acids per se are less desirable for use as the proteinaceous material because they will generally not be large enough to bridge the molecular spacing between reactive portions of the hair (e.g., the cysteines moieties) to form desired cross-links. Accordingly, it is preferred that the proteinaceous material not be only amino acids per se; however, amino acids can be used as part of the proteinaceous material provided that the proteinaceous material comprises larger molecules (e.g., peptides, polypeptides, and proteins) that can form the desired cross-links involving the keratin of the hair. If amino acids per se are present, desirably they comprise no more than 50% by weight of the total proteinaceous material, more desirably no more than 40%, most desirably no more than 30%, preferably no more than 20%, more preferably no more than 10%, and most preferably no more than 5%.

The cysteine in the hair, e.g., resulting from the cleavage of the disulfides of cystine of the hair's keratin (the cleavage occurring naturally or as a result of the use of waving solution), will be the principal part of the keratin in the hair participating in the reformation of cystine. About half of the cystine is in the cuticle of the hair and the other half is in the cortex of the hair. That is why it is important that at least some of the active ingredients of the first and second compositions of this invention (that is, the at least one preferably polyvalent metal, the optional proteinaceous material, and the optional acid) be able to penetrate and actually do penetrate the hair so that the cysteine in the cortex (in addition to the cysteine in the cuticle) can participate in formation of the disulfide bonds involving the keratin of the hair. Hence the preference that the proteinaceous material contain a significant number of molecules having a molecular weight of about 2,000 or less regardless of the actual average molecular weight of the proteinaceous material. The metals and the acids will almost always be small enough so that penetration of enough of each of them into the hair will not usually be a problem.

Without wishing to be bound by any theory, it is believed that the protein in the compositions of the invention, which are applied while residual reducing agent remains in the hair, helps protect the hair by reacting with the residual reducing agent (particularly if the compositions contain keratin protein), thereby decreasing the amount of residual reducing agent on and in the hair that can react with the hair.

The pH of the compositions of this invention will usually be at least 1 and usually 10 or less, typically 6.0 or less, desirably 5.5 or less, more desirably 5.0 or less, preferably 4.5 or less, more preferably 4.0 or less, and most preferably 3.5 or less. (A pH less than about 2 may pose safety problems and rarely will be used but in some cases it may be possible.) Thus, the pH will usually range from 1 to 10, typically from 1 to 6, desirably from 2 to 5, more desirably from 2 to 4.5, and preferably from 2 to 3.5.

The pH of the first composition will preferably be from about 2 to about 3.5. The target pH of the hair after application of the first composition is about 4.5 to 5.5. The pH of the second composition will preferably be from about 3.3 to about 4.3. The target pH of the hair after application of the second composition is that sufficient to result in effective color deposit and will generally be in the range of about 4.5 to 5.5. The specific pH of a particular composition will depend on its intended use. For example, the pH of one preferred first composition will typically be about 2 and the pH of one preferred second composition will typically be about 3.5 (regardless of the targeted color level). Higher or lower pH values may be used in a particular case provided the benefits of this invention can still be achieved.

Depending on the particular metal(s)/metal compound(s) and proteinaceous materials used, each of the first and second compositions of this invention containing them may have a pH within the desired range for the intended use, in which case it may not be necessary to add a pH-adjusting agent such as an acid to the composition.

If an acid must be included in a composition to reduce the pH to the desired level, any acid may be used. Carboxylic acids are preferred because they are generally not fully dissociated in water and act in essence to buffer the composition at the desired pH. On the other hand, mineral acids (and some organic acids) are usually fully dissociated in water and will not provide the buffering effect. Accordingly, if acids are used that fully dissociate in water, buffering agents may be needed to maintain the pH at the desired level. The mineral acids that may be used include sulfuric and hydrochloric.

Acids such as acetic acid, propionic acid, and particularly hydroxycarboxylic acids such as lactic acid, glycolic acid, tartaric acid, malic acid, citric acid, and glucolic acid may be used, of which acetic and citric are preferred and citric is most preferred. Citric acid is believed to crystallize in the hair and thereby stiffen it.

The acids can be used in their acid form or in their salt form, e.g., their alkali metal salt form. Thus as used herein, the terms "an acid" or "an acid selected from the group consisting of carboxylic acids and mineral acids" should be understood to include their salts that when used in the composition of this invention will help provide the desired pH adjustment. When such an acid salt is used, additional acidic material may be required to provide a pH below about 4. The cost and availability of the various acids and acid salts will help determine which are used in the composition.

The amount of acid added to the composition will range from none (if the pH is already at the desired level) up to about 6.5% by weight of the composition, usually from about 0.001% to about 5% by weight of the composition, and more often from about 0.01% to about 3% by weight of the composition, and preferably from about 0.5% to about 2.5%.

Because it is desired that sufficient amounts of each of the "major ingredients" used in each of the first and second compositions of this invention (the metals, usually in the form of polyvalent metal compounds, the optional but preferred proteinaceous materials, and the optional acid) penetrate the hair fibers and that their presence ultimately results in the formation of sufficient disulfide bonds involving the keratin of the hair, it is important that the composition not contain excessive amounts of "hindering materials," by which is meant materials that because of their nature (e.g., hydrophobicity, film-forming tendency, adverse reactivity) prevent sufficient penetration of the major ingredients into the hair to achieve the benefits of this invention and/or prevent sufficient formation of disulfide bonds involving the keratin of the hair to achieve the benefits of this invention. Ideally each of the two compositions should contain no substance that forms a significant barrier to penetration into the hair fibers of the composition and its major ingredients (e.g., forms a significant barrier by coating the hair) and prevents sufficient formation of disulfide bonds involving the keratin of the hair.

"Hindering materials" can include polyhydroxyalcohols (e.g., glycerine, glycols), hydrophobic materials (e.g., mineral oils, silicones, fatty acids (for example, vegetable oils, safflower oil, oleic acid)), heavy metals that can break down peroxides, mineral thickeners (e.g., V-Gum, bentonite, and other clay and clay-like derivatives), some emulsifying agents (e.g., cetyl alcohols, stearyl alcohol), thickeners (e.g., cellulose gums in high concentrations; cellulose gums in low concentrations may be used unless they are in emulsions), mineral waxes (e.g., paraffins, ozocerites), and film-forming polymers (e.g., acrylics, styrene resins).

The total amount of hindering materials, if present, will usually be not greater than 10% by weight of each composition, more typically not greater than 5%, desirably not greater than 2%, more desirably not greater than 1%, most desirably not greater than 0.5%, preferably not greater than 0.25%, more preferably not greater than 0.1%, most preferably not greater than 0.01%, and sometimes not greater than 0.001% by weight of each composition. The amount and types of hindering materials that can be present without significantly adversely affecting the ability to achieve the benefits of the invention will depend on the particular composition.

If the first or second composition does contain a substance that tends to coat the hair fibers, the substance desirably is non-ionic because ionic materials tends to further inhibit the penetration of the composition and major ingredients. Hair is hydrophobic and each of the first and second compositions used in the process of this invention is typically an aqueous composition (e.g., an aqueous solution). Therefore, if excessive amounts of cationic materials are added to such a composition used in this invention, the cationic materials will tend to make it even more difficult for the composition to penetrate the hair fibers because the cationic materials will tend to repel the composition from the hair fibers.

For comparison, commercially available conditioner compositions often contain about 1.5 to 5% cationic materials, which are designed to stay on the outside of the hair fibers. Hair tends to "like" oils but oils also tend to inhibit the necessary penetration of the composition of this invention into the hair fibers. Other substances that are often found in commercially available hair treating compositions include silicones, thickeners (e.g., gums, polyglycols), and fragrances and may also pose a problem. Regardless of the nature and/or concentration of other ingredients in the composition of this invention, they should not prevent sufficient penetration of either of the compositions into the hair fibers or prevent the advantages of this invention from being realized.

Generally, at least 10% of each of the at least one metals (typically in the form of polyvalent metal compounds), the optional proteinaceous materials, and the optional acid of the first and second compositions will be able to penetrate the hair within an hour. Desirably, at least 20% of each will be able to penetrate the hair within an hour. More desirably, at least 30% of each will be able to penetrate the hair within an hour. Preferably, at least 40% will be able to penetrate the hair within an hour. More preferably, at least 50% will be able to penetrate the hair within an hour. In some cases, significantly more that 50% of each will be able to penetrate the hair within an hour. Generally speaking, the major ingredients of this composition will be carried into the hair fiber by and along with the carrier (preferably aqueous) that is used.

The compositions used in the process of the invention can contain additives provided they do not significantly adversely affect the compositions and their functioning (e.g., reduce penetration of the major ingredients into the hair fiber below the minimum required) so as to prevent the advantages of this invention from being achieved. The additives are not generally required to obtain the advantages of the invention but the efficacy, shelf-life, ease of application, and organoleptic properties of the invention can be improved by the presence of small amounts of the additives. Additives will usually be present in concentrations not exceeding about 25% (preferably not exceeding 15%) by weight of the composition in question although higher levels can be used in specific cases. The additives that can be used include fragrances, colorants, preservatives, viscosity control agents, penetration assistants (penetrants), water-miscible solvents, and wetting agents (surfactants) and are materials that are well-known in the art.

Fragrances and colorants may be added to improve the organoleptic and aesthetic properties of each composition for the consumer. The fragrances impart a pleasant odor or aroma to the product. The colorant can be included in each composition to provide the composition with a uniform attractive color and appearance.

When the pH of a composition used in the process of the present invention is towards the lower end of the pH range, a preservative usually will not be required because such pH values are biocidal or at least biostatic for organisms such as fungi, yeast, and bacteria. However, when the pH of the composition is towards the upper end of the pH range, it may be necessary to include preservatives in the composition so that it will have a useful (sufficiently long) shelf-life. Useful preservatives include methylparaben, ethylparaben, propylparaben, and butylated hydroxytoluene ("BHT").

The first and second compositions can contain viscosity control agents or thickeners to improve the ability of each composition to coat and cling to the hair fiber for a sufficient length of time (e.g., so that the major ingredients can penetrate the hair to the extent necessary and so that disulfide bonds can be formed in the cortex and cuticle of the hair fiber). As noted above, the viscosity control agents and thickeners should not prevent the required penetration of the major ingredients. The viscosity control agents and thickeners are generally polymeric materials and are well-known in the hair treatment art.

Penetrants can be included in each composition to increase the rate at which the composition penetrates the hair. The penetrants are generally water-miscible solvents that enhance the ability of the composition to penetrate the hair. Penetrants are well-known materials in the art.

Wetting agents (surfactants) may also be used in the compositions used herein. Wetting agents increase the rate at which the compositions spread over the hair surface. If the hair surface is wetted at a faster and more uniform rate, the probability for more even treatment is enhanced.

As discussed above, acid (including acid salt) may be required to adjust the pH to the desired range if the composition in question without the acid does not otherwise have the desired pH. However, it may also be advantageous to add non-acid materials to the composition to adjust the pH. Thus, it should be understood that the additives that can be employed in the composition of the present invention include such other non-acid pH-adjusting substances, e.g., alkali substances. Preferred alkaline substances to adjust the pH of the composition are the alkali metal hydroxides and ammonium hydroxide.

Buffering agents may be added to maintain or help maintain the pH of the composition at the desired level.

A mixture comprising the major ingredients and any additives of each of the first and second compositions can be prepared in a concentrated form and then diluted with water to form the first and second compositions. Concentrates are useful because their use reduces packaging, handling, storage, and shipping costs. Each of the first and second compositions may also be prepared as a two-package system with some of the ingredients of the composition in one package and the remaining ingredients in a second package. That two-package system may be useful in cases where the total composition in a single package does not have as long a shelf-life as the two separate partial compositions in two packages.

When each of the first and second compositions is applied to hair, the composition should be applied to cover substantially all of the hair fibers. The method of application is to some degree dependent on the arrangement of the hair at the time of application. Methods of applying treating liquids to hair are well-known in the art. The compositions can be applied by blotting, misting, dipping, squeegeeing, or by using other methods known in the art, e.g., using a "snip top" applicator bottle. The method of application is not critical provided the composition is applied so as to coat substantially all of the hair fibers.

A preferred first composition (perm deactivator) for the process of this invention is aqueous and has the following composition: 15% by weight Epsom salt ($MgSO_4.7H_2O$), which is equivalent to roughly 7.5% by weight magnesium sulfate or roughly 1.5% magnesium; 0.4% by weight CROTEIN WKP and 0.3% by weight CROQUAT WKP, which together equals about 0.178% proteinaceous material or roughly 182 ppm cystine; 0.2–0.25% solubilizing agent and fragrance (e.g., a mixture of two fragrance compositions marketed by Carruba, namely, Gardenia Fragrance No. A5462 and Citrus Fragrance No. A5224 in a 9/1 ratio); citric acid to bring the pH to 2; and sufficient water to bring the total to 100%.

A preferred second composition (color builder) for color levels 1–6 for the process of this invention is aqueous and has the following composition: 10% by weight Epsom salt ($MgSO_4.7H_2O$), which is equivalent to roughly 5% by weight magnesium sulfate or roughly 1% magnesium; 1.5% by weight CROTEIN WKP and 1.5% by weight CROQUAT WKP, which together equals about 0.78% proteinaceous material or roughly 796 ppm cystine; 0.3–0.35% solubilizing agent and fragrance (e.g., a mixture of two fragrance compositions marketed by Carruba, namely, Gardenia Fragrance No. A5462 and Citrus Fragrance No. A5224 in a 9/1 ratio); citric acid to bring the pH to 3.5; and sufficient water to bring the total to 100%.

A preferred second composition (color builder) for color levels 7 and higher for the process of this invention is aqueous and has the following composition: 3–4.5% by weight Epsom salt ($MgSO_4.7H_2O$), which is equivalent to roughly 1.5–2.25% by weight magnesium sulfate or roughly 0.3–0.45% magnesium; 1.5% by weight CROTEIN WKP and 1% by weight CROQUAT WKP, which together equals about 0.63% proteinaceous material or roughly 643 ppm cystine; 0.3–0.35% solubilizing agent and fragrance (e.g., a mixture of two fragrance compositions marketed by Carruba, namely, Gardenia Fragrance No. A5462 and Citrus Fragrance No. A5224 in a 9/1 ratio); citric acid to bring the pH to 3.5; and sufficient water to bring the total to 100%.

Broadly speaking, the same-day waving and coloring process of this invention comprises: optionally shampooing the hair; wrapping the hair on forming members (e.g., rods), if the hair is to be curled; applying a waving solution to hair and processing according to the manufacturer's recommendations; optionally removing excess waving composition, desirably without rinsing (e.g., by blotting), after the waving composition has relaxed the hair to the required degree; applying the first composition of the invention to the hair and scalp to saturate the hair; allowing that composition to remain in contact with the hair for a sufficient time; removing excess first composition without rinsing (e.g., by blotting); applying the second composition to the hair and scalp to saturate the hair; without any intervening blotting, drying the hair by heating the hair at medium heat (at about 105° F., which is about 40° C.) so that substantially all of the hair is substantially dry; applying coloring composition (e.g., oxidative dye and oxidizing agent) to the hair and processing according to the manufacturer's recommendations; optionally applying more oxidizing agent (e.g., hydrogen peroxide) to the hair; if the hair is on forming members, removing the hair from the forming members (e.g., rods); and optionally shampooing the hair.

The combined same-day waving and coloring process of this invention usually starts with a shampoo to remove material (e.g., oils) from the hair that could interfere with the activity of the waving composition and/or the compositions of this invention. Scalp manipulation should be avoided to minimize irritation.

If desired, a "pre-wrap" may then be applied. A "pre-wrap" is sometimes used on previously processed hair just prior to applying the reducing solution in a permanent waving process. The pre-wrap treatment is thought to reduce the porosity of the hair and protect the hair from many of the damaging effects of the permanent waving reducing solution and achieve stronger, springier, more helically shaped curls in processed hair.

The pre-wrap composition can be applied on shampooed towel-blotted hair so that the hair is wet but not dripping. The hair is combed to distribute the pre-wrap composition throughout the hair and allowed to remain on the hair for at least 1 minute prior to beginning the permanent wave wrap (i.e., the wrapping of the hair on forming members, if the hair is to be curled).

Any pre-wrap composition may be used. Preferred compositions are disclosed in PCT Patent Application No. PCT/US95/11649 and may comprise 1% $MgSO_4.7H_2O$, 0.35% fragrance (a mixture of Gardenia Fragrance No. A5462 and Citrus Fragrance No. A5224 in a 9/1 ratio), 1.5% of a mixture of CROTEIN WKP and CROQUAT WKP in a weight ratio of 4 weight units of CROTEIN WKP to 3 weight units of CROQUAT WKP, and sufficient citric acid and/or other pH-adjusting additives to give a pH of 4.5 to 5.5.

If the hair is to be curled, the hair is wound on rods (i.e., wrapped) to provide the mold for the curl size and shape. Picks are used and a highly viscous, biologically acceptable, non-reactive substance (e.g., a petroleum jelly such as that marketed under the mark VASELINE) is applied around the hairline along with a cotton coil. All of this is well-known in the art.

Waving composition (reducing solution) is then applied to the hair and permitted to remain in contact with the hair for a sufficient time to relax the hair, i.e., reduce (and thereby disrupt or break) a sufficient number of chemical (disulfide) bonds within the hair to permit the hair to relax (i.e., stop fighting against) and remain in the new arrangement or configuration. Relaxation of the hair results in softening the feel of the hair but also weakens the hair. If the hair is to be straightened and not curled, the hair is combed while in contact with the waving composition. Hair contacted with the waving (reducing) agent to reduce a portion of the disulfide bonds in the hair may be referred to as "reduced hair." Desirably the reduced hair will have a sufficient number of reduced (disrupted or broken) chemical (disulfide) bonds within the hair to permit the hair to remain in the desired arrangement or configuration.

Any waving agent may be used so long as the advantages of this invention can be achieved. Typically the waving agent will be a sulfur-containing material, e.g., a thioglycolate.

During contact with the waving composition, the hair can be heated to increase the rate at which the bonds are disrupted and the hair relaxed. The temperature and length of time during which the waving composition is contacted with the hair is dependent upon the components in the waving composition, and the manufacturer's recommendations are followed. Contact time is usually from 3 to 30 minutes.

It is generally believed to be critical to achieving a successful permanent wave that as much of the waving composition as possible be removed from the hair, both that on the surface of the hair fibers and that which has penetrated into the hair fibers, after the hair has been softened and shaped to the required degree (i.e., after a sufficient number of chemical bonds have been cleaved). This belief arises from several facts, including the fact that the waving composition is usually at a pH higher than that of the neutralizing (oxidizing) composition (which is typically acidic) and that excessive waving composition (a reducing agent) left on the hair can react with the neutralizing (oxidizing) agent and thereby reduce its effectiveness. Reduced rebonding effectiveness is detrimental because it reduces the number of disulfide bonds that can be formed to hold the hair in the desired new arrangement or configuration.

After processing with the waving solution is complete (i.e., the desired amount of bond-breaking or relaxation has occurred), the reduced hair should be blotted immediately (e.g., with cotton towel, which will take about 1 minute) and then the picks removed and the hair (including the hair at the scalp) blotted thoroughly (e.g., with paper towels), preferably rod-by-rod, for about 3 minutes or until there is little or no residual wetness. A fresh cotton coil should then be substituted for the original one. It is important to remove as much of the waving solution (which contains the reducing agent) as possible. Removing as much as possible will permit more rapid contact and more rapid penetration of the first composition into, and therefore reaction of the first composition with, the hair. Removing as much as possible will also tend to help reduce skin and scalp irritation.

Desirably blotting is sufficient and the waving solution is not rinsed from the hair, thereby avoiding the problems caused by rinsing at this time. The compositions of the process of this invention make such rinsing unnecessary while still providing superior waving and coloring results and improved hair properties.

The first composition ("perm deactivator") is then applied directly to the hair and scalp to saturate the hair (e.g., on the typical head using 3 to 4 ounces, which is about 90 to 120 cc, or more, particularly for longer hair). The composition is preferably applied so that the composition contacts each hair fiber that has been treated with the waving composition to try to deactivate residual reducing agent. It is important that the first composition also contact the scalp completely (e.g., to help reduce possible skin and scalp irritation). Thorough coverage with the first composition can be achieved using any technique, including the techniques noted above.

The first composition is permitted to remain in contact with the hair and scalp for at least 1 minute and preferably for 2 minutes or more after its application to the hair is completed.

Preferably the first composition is at a highly acidic pH, e.g., a pH of 2, and it contains proteinaceous material containing cystine. The highly acidic pH helps inactivate the waving solution, which typically is active at an alkaline pH. In addition, and without wishing to be bound by any theory, it is also believed that at least some of the residual waving solution in the hair reacts with some of the cystine that is preferably present in the first solution. That would produce cysteine moieties, which according to this process will remain in the hair and help rebonding. Despite this, some unreacted waving compounds (e.g., thioglycolate) will remain in the hair.

The hair is then blotted (e.g., with cotton towel) and then (including the hair at the scalp) thoroughly blotted (e.g., with paper towels), preferably rod-by-rod, for about 3 minutes or until there is little or no residual wetness.

Although in some cases it may be possible to use one composition rather than two in the process of the present invention, it is preferred that a second composition be used and that it be applied at this time. This second composition ("color builder"), which typically will have a different composition and pH than the first composition, is applied directly to the hair and scalp to saturate the hair (e.g., on the typical head using 3 to 4 ounces, which is about 90 to 120 cc, or more, particularly for longer hair). The composition is preferably applied so that the composition contacts each hair fiber. It is important that the second composition also contact the scalp completely (e.g., to help reduce possible skin and scalp irritation). Thorough coverage with the second composition can be achieved using any of the techniques noted above. This second composition should not be removed from the hair or scalp, so there should be no blotting.

As noted, in some cases it may be possible to omit the use of any second composition and have the first composition perform all of the functions. However, it usually will be preferable to use both the first and the second compositions. One obstacle to using only the first composition and dispensing with the optional second composition is that, generally speaking and with typical waving and alkaline coloring compositions used in the process, the pH of the composition used after waving (reduction) should be low enough to help halt the action of the reducing agent and the pH of the composition used just before the drying and coloring should not be as low. That is why the pH of the preferred first composition is about 2 and the pH of the preferred second composition is preferably about 3.5. If only the preferred first composition (pH of about 2) is used, the color provided by the process may suffer. On the other hand, if only one composition having a pH of about 3.5 is used, the curl may suffer.

The hair is then dried, preferably by heating, so that substantially all of the hair is substantially dry. Thus, the hair is being dried while it is still on the forming members (if the hair has been placed on forming members) and while residual waving solution (containing, e.g., thioglycolate), residual first composition, and optional second composition remain in the hair. The drying evaporates the carriers (typically water) from the various liquid compositions and dries the non-volatile moieties in those compositions (e.g., thioglycolate or other waving agent, metals, proteinaceous materials, and pH-adjusting agents) onto and into the hair (a significant portion of those moieties have entered each individual hair strand during the earlier steps of the process).

By "substantially all of the hair is substantially dry" is meant that substantially all (usually at least 85%, desirably at least 90%, more desirably at least 95%, most desirably at least 98%, preferably at least 99%, more preferably essentially all, and most preferably 100%) of the hair will at the least be dry to the touch in contradistinction to wet or even slightly damp to the touch. The required drying cannot be achieved merely by blotting, even by thorough blotting, because insufficient moisture will be removed, particularly from the hair closest to a forming member if the hair is on forming members. Thus, the average moisture content of the hair will typically be less than 20% by weight, usually less than 15%, desirably less than 10%, more desirably less than 7.5%, most desirably less than 6%, preferably less than 5%, more preferably less than 4%, most preferably less than 3%, and in some cases less than 2% or even 1%. To insure that substantially all of the hair is substantially dry, particularly when the hair is on forming members (e.g., rods), one or two test curls are taken. Thus, if the hair is on rods/curlers, one or two "test curls" are taken (i.e., by dropping the rod and inspecting the hair) to confirm that the innermost coil of hair is dry. In addition, if an end paper is used and the end paper is dry, this drying step in complete.

This drying step may be carried out at medium to high heat using a hooded dryer or other source of even heat. If too much moisture remains in the hair, and particularly if the hair is not uniformly at the same moisture/dryness level, the coloring composition will not be taken up evenly by the hair during the subsequent coloring portion of the process and uneven coloring of the hair will result. This drying step will typically take at least 5 minutes, often at least 8 minutes, sometimes 12 minutes, or even substantially longer, depending on the length, thickness, and initial moisture content of the hair and on the drying/heating method used.

A surprising feature and advantage of the invention is that the hair can be subjected to such heat, particularly for a long period of time (to substantially dry substantially all of the hair) while residual waving agent (e.g., thioglycolate) is present in and on the hair. Without the process of this invention, hair in this condition (containing residual waving agent) subjected to such heat could be seriously adversely affected.

Without wishing to be bound by any theory, it is believed that this heating encourages, among other things, air oxidation (i.e., rebonding), reaction (i.e., destruction) of the residual reducing agent on and in the hair, and, if the hair is on forming members, shrinkage of the hair on the forming members, resulting in a curl that is tighter and truer to the size of the forming members.

In the next (coloring) phase of the process, a large enough batch of commercial color is mixed (more is needed because the color will be applied to all of the hair and not just the new growth). When using a more viscous coloring composition (e.g., a product marketed by Matrix under the mark SO-COLOR), a clear developer and a bullet shaker or applicator is desirably used for mixing.

The coloring composition contains an oxidative dye (preferably permanent but also semi-permanent) and an oxidizing agent. The oxidative dyes are well-known, and any such dye may be used in the process of this invention provided the benefits of this invention can be achieved. The oxidizing agent typically will be hydrogen peroxide, but any oxidizing agent can be used provided the benefits of this invention can be achieved. If hydrogen peroxide solution is used, typically a twenty volume solution will be employed except for the ultra-light colors, in which case a thirty volume solution can be employed. It is another surprising feature and advantage of this invention that for the ultra-light colors a thirty volume solution can be used, because ultra-light colors typically require a forty volume peroxide solution.

It may be beneficial to apply the coloring composition first to the new growth. When that has been accomplished, the coloring composition may then be applied as a touch-up to the rest of the hair using normal timing. If the hair is on forming members (e.g., rods), it is best to apply the coloring composition first to the new growth and then to the hair on the rods. The bands should be turned 180° and additional coloring composition can then be applied to the hair on the forming members, including the newly exposed band areas and also to the hair on the underside of the forming members. Coloring composition that has not been applied to the hair should be reserved for possible use in a later step of this process. If the person whose hair is being processed experiences any tingling of the scalp after the coloring composition has been applied, cool air, e.g., from a cool dryer (using only the fan) or from a blower, should immediately be blown onto the person's hair and scalp until the tingling subsides.

The cotton coil should be replaced, while being careful not to position the cotton on any hair (because the cotton would absorb some of the coloring composition from the hair).

The color is then allowed to develop in the hair. Typical processing time is 20–40 minutes. For example, for the SO-COLOR product, processing time is about 30 minutes. For a product marketed under the mark LOGICS, processing time is about 25 minutes. Generally speaking, this processing time will be the standard processing time for the coloring composition when it is not being used in the combined waving/coloring process of this invention.

As noted above, in a preferred process, residual reducing agent, e.g., thioglycolate, a sulfurous material, is not rinsed from the hair and therefore is dried onto and into the hair by the drying step. Accordingly, the residual reducing agent is still present on and in the hair at the time the coloring composition is applied. Successful coloring results are surprising in view of the fact that the art teaches that oxidative dyestuffs should not be used in the presence of sulfurous materials because "oxidative dyestuffs are irreversibly altered in their color upon contacting sulfurous materials, such as are found in the permanent waving compositions" (U.S. Pat. No. 5,188,639, column 3, lines 5–13).

The oxidation agent, e.g., hydrogen peroxide, applied as part of the coloring composition to develop the color will at this time also be functioning as a waving neutralizer (oxidizing agent) to reform cystine bonds (the disulfide bonds), i.e., to reform that part of the keratin. If hydrogen peroxide is used, it typically will be in a 3% or less aqueous solution, although in some cases with the present process, lower concentrations may be used.

In a standard waving process, the neutralizer (oxidation agent) is contacted with the hair to reform the bonds for only a few minutes (e.g., typically 5–8 minutes) to avoid the damage to the hair that occurs if the contact time is significantly increased. However, as noted above, in the present process the standard substantially longer color development times recommended by the manufacturers of the hair color preparations (e.g., from about 20 to about 40 minutes) may successfully be used.

That is another surprising feature and advantage of this invention, namely, that the double-functioning oxidizing agent added as part of the coloring composition may be left in contact with the hair for a much longer period of time than that normally recommended by manufacturers of waving compositions. The longer neutralization time provides a more complete neutralization (oxidation or rebonding) and without excessive damage to the hair. As a result of the additional neutralization time, the hair has springier and tighter curls than hair that has been treated by a conventional process. The longer contact time is possible with the process of the present invention in part because the first and second compositions protect the hair from the damaging effects of the oxidizing agent in the coloring composition.

After the required color development time, optional additional oxidizing agent ("sealer") is contacted with the hair, typically in the form of an aqueous solution, for up to about 10 minutes but longer times may be used. A preferred solution is 1.5% hydrogen peroxide solution, and from 2 to 4 ounces (about 60 to 120 cc) or more, particularly for longer hair, will be used for the typical head. This step is optional but preferred, particularly with paste coloring compositions or if a viscosity-reducing agent is not employed for the coloring composition. The sealer helps ensure neutralization of the waving (reducing) agent (i.e., rebonding), particularly at the ends of the hair, which might otherwise not occur to a sufficient extent if the hair is long and/or is on forming members and/or the viscosity of the coloring composition is too high.

The hair is then rinsed and shampooed in normal fashion, preferably with a buffered shampoo (e.g., an equal mixture of mild shampoo and light conditioner), and then conditioned.

Another surprising feature and advantage of the process of this invention is that with this process, hair being curled by being wrapped on forming members can successfully be colored while it is still on the forming members. To applicant's knowledge, the present process is the first same-day (one-session) waving/coloring process that results in the hair having good properties, wave, and color.

A number of experiments were run using different compositions. In a first set of experiments, hair samples were treated using the preferred process of this invention with the hair on rods (for curling) and keeping all parameters constant from run to run except for the type and concentration of metal compound used in the second composition. Various properties of the resulting hair from each run were rated on a scale from 1 (worst) to 5 (best), with a rating of 5 being given for each property of the hair treated with the preferred second composition, which thus acted as the control (in the preferred second composition, magnesium is the metal and it is furnished by Epsom Salt, which is $MgSO_4 \cdot 7H_2O$). In general, the concentration of each metal compound was adjusted to try to give the same color strength as the control, i.e., a color strength rating of 5. The pH of all second compositions was adjusted with citric acid to be 3.5. Results are shown in the following table ("nr" means not rated).

TABLE 1

| Compound | Conc. (wt. %) | Color Strength | Color Tone | Evenness of Tone | Grey Coverage | Evenness of Coverage |
|---|---|---|---|---|---|---|
| $MgSO_4 \cdot 7H_2O$ (control) | 10.0 | 5 | 5 | 5 | 5 | 5 |
| Aluminum Sulfate | 0.06 | 5 | 4 | 5 | 3 | 4 |
| Aluminum Sulfate | 0.3 | nr | 1 | nr | 5 | nr |
| Potassium Acetate | 1.75–2.25 | 3.5 | 3 | 1 | 3 | 1 |
| Aluminum Chloride | 0.13 | 5 | 3 | 5 | 5 | 5 |
| Aluminum Sulfate | 10.0 | 3.5 | 3 | 4 | 4 | 4 |
| Zinc Acetate | 0.02 | 4 | 4 | 3 | 2 | 3 |
| Magnesium Acetate | 3.9 | 3.5 | 3 | 2.5 | 3 | 4 |
| Calcium Acetate | 2.0 | 4 | 4 | 1 | 3 | 3 |

If the hair is on forming members, the hair is removed from them. The hair is then manipulated for about 5–10 minutes or more to insure complete dispersion throughout the hair of the coloring composition, which has not yet been removed from the hair. Complete dispersion of the coloring composition, which contains the double-functioning oxidizing agent, is important for several reasons, including encouraging evenness of color and encouraging as much rebonding as possible (thereby improving curl properties). In addition, for long hair, some of the coloring composition that was reserved from earlier in the process is preferably applied to the hair, particularly to the ends. With short hair, such added reserved coloring composition may not be necessary.

Results for the other hair properties ("liftability," hair condition, shine, richness) varied. (By "liftability" is meant the ability of the color level to be raised by the process.) All of the compositions yielded hair condition and shine that rated either 4 or 5, compared to 5 for the control; the values for richness ran from 3 to 5. In particular, aluminum sulfate at 0.06% resulted in a liftability of 4 and hair condition, shine, and richness values of 5.

In a second set of experiments, the preferred process was run with the preferred first and second compositions but with substitution of various proteinaceous materials in the preferred first composition for the 0.4% CROTEIN WKP and 0.3% CROQUAT WKP and in the preferred second composition for the 1.5% CROTEIN WKP and 1.5% CRO-QUAT WKP (for color levels 1–6) and without using any sealer (i.e., the additional oxidizing agent, e.g., 1.5% hydrogen peroxide, which may be applied after color processing and before the hair is removed from any forming members). Hair processed using this process and preferred first and second compositions (the control; last row of Table 2) rated excellent in both curl and color after the process was completed as well as after shampooing the hair three times. Each of the following proteinaceous materials was substituted for all of the proteinaceous materials in both the first and second compositions, giving the results shown in Table 2 for the curl and color of the hair after the process was completed and after shampooing three times: HYDROTRITICUM 2000 (hydrolyzed vegetable protein derived from whole wheat), CROQUAT M (cocodimonium hydrolyzed protein), HYDROSOY 2000/SF (hydrolyzed soy protein), and CROSILQUAT (cocodimonium silk amino acids). In Table 2 and in the tables that follow, "E" means a rating of excellent, "VG" means a rating of very good, "G" means a rating of good, "F" means a rating of fair, and "P" means a rating of poor; "/" between two ratings indicates a result between the two ratings indicated. "Comps. 1 & 2 Proteinaceous Material" indicates the proteinaceous material that was used in both the first and second compositions.

TABLE 2

| Comps. 1 & 2 Proteinaceous | Ratings After Process | | Ratings After Three Shampoos | |
|---|---|---|---|---|
| Material | Curl | Color | Curl | Color |
| HYDROTRITICUM 2000 | F | F/P | P | P |
| CROQUAT M | F/P | F/P | P | P |
| HYDROSOY 2000/SF | F/P | F/P | P | P |
| CROSILQUAT | F/P | F/P | P | P |
| CROTEIN WKP & CROQUAT WKP | E | E | E | E |

Without wishing to be bound by any theory, it is believed that the higher cystine contents of the first and second preferred compositions (each using a mixture of CROTEIN WKP and CROQUAT WKP) as compared to the cystine contents of the first and second compositions when using the other proteins is a principal reason for the superior results obtained with the preferred first and second compositions.

In a third set of experiments, the preferred process was run with the preferred first composition but with substitution of various proteinaceous materials in the preferred second composition for the 1.5% CROTEIN WKP and 1.5% CROQUAT WKP (for color levels 1–6) and without any sealer (i.e., the additional oxidizing agent, e.g., 1.5% hydrogen peroxide), giving the results noted in Table 3. In Table 3, the heading "Comp. 2 Proteinaceous Material" indicates the proteinaceous material used in the second composition.

TABLE 3

| Comp. 2 Proteinaceous | Ratings After Process | | Ratings After Three Shampoos | |
|---|---|---|---|---|
| Material | Curl | Color | Curl | Color |
| HYDROTRITICUM 2000 | G/F | G/F | F | F |
| CROQUAT M | F | F | F | F |

TABLE 3-continued

| Comp. 2 Proteinaceous | Ratings After Process | | Ratings After Three Shampoos | |
|---|---|---|---|---|
| Material | Curl | Color | Curl | Color |
| HYDROSOY 2000/SF | F | F | F | F |
| CROSILQUAT | F | F | F | F |
| CROTEIN WKP & CROQUAT WKP | E | E | E | VG |

Hair processed using the preferred first and second compositions (the control; last row of Table 3) rated excellent in curl and color after the process was completed, excellent in curl after shampooing the hair three times, and very good in color after shampooing the hair three times. Substitution of the other proteinaceous materials for the preferred CROTEIN WKP and CROQUAT WKP in the second composition significantly reduced the curl and color of the hair.

In a fourth set of experiments, the preferred process was run with the preferred second composition but with substitution of various proteinaceous materials in the first composition for the preferred mixture of 0.4% CROTEIN WKP and 0.3% CROQUAT WKP and again without any sealer (i.e., the hydrogen peroxide solution applied after color processing and before removing the hair from any forming members). The results are shown in Table 4, and the heading "Comp. 1 Proteinaceous Material" indicates the proteinaceous material used in the first composition.

TABLE 4

| Comp. 1 Proteinaceous | Ratings After Process | | Ratings After Three Shampoos | |
|---|---|---|---|---|
| Material | Curl | Color | Curl | Color |
| HYDROTRITICUM 2000 | G | F | G/F | F |
| CROQUAT M | G | F | G/F | F/P |
| HYDROSOY 2000/SF | G | F | G/F | F/P |
| CROSILQUAT | G | F | G/F | F/P |
| CROTEIN WKP & CROQUAT WKP | E | E | E | E |

Hair processed using the preferred first and second compositions rated excellent in both curl and color after the process was completed as well as after shampooing the hair three times. Substitution of the other proteinaceous materials for the preferred proteinaceous materials in the first composition resulted in a significant reduction in the quality of the curl and color after the process was completed and after three shampooings, but the reduction was generally not quite as severe as when the preferred first composition was used and the proteinaceous material in the second composition was varied (Table 3).

In a fifth set of experiments, the preferred process was run with the preferred first and second compositions but with substitution of various proteinaceous materials in the preferred first composition for the 0.4% CROTEIN WKP and 0.3% CROQUAT WKP and in the preferred second composition for the 1.5% CROTEIN WKP and 1.5% CROQUAT WKP (for color levels 1–6) and with sealer (1.5% hydrogen peroxide, applied after color processing and before the hair is removed from the forming members). In other words, this fifth set of experiments was essentially the same as the second set (reported above) with the addition of sealer. The results are shown in Table 5.

TABLE 5

| Comps. 1 & 2 Proteinaceous | Ratings After Process | | Ratings After Three Shampoos | |
|---|---|---|---|---|
| Material | Curl | Color | Curl | Color |
| HYDROTRITICUM 2000 | G | G | G | F/G |
| CROQUAT M | G | G | G | F/G |
| HYDROSOY 2000/SF | G | G | G | F/G |
| CROSILQUAT | G | G | G | F/G |
| CROTEIN WKP & CROQUAT WKP | E | E | E | E |

Hair processed using the preferred first and second compositions and the sealer (the control; last row of Table 5) rated excellent in both curl and color after the process was completed as well as after shampooing the hair three times. Substitution for the proteinaceous materials in both the first and second compositions resulted in significant reduction in the ratings but, as revealed by comparing these results shown in Table 5 with the generally poorer results shown in Table 2, the effect of the substitution was ameliorated by using the sealer.

In a sixth set of experiments, the preferred process was run with the preferred first composition but with substitution of various proteinaceous materials in the preferred second composition for the 1.5% CROTEIN WKP and 1.5% CROQUAT WKP (for color levels 1–6) and with sealer (1.5% hydrogen peroxide solution), giving the results noted in Table 6. Thus, the runs reported in Table 6 were essentially the same as the runs reported in Table 3 except for the addition of the sealer.

TABLE 6

| Comp. 2 Proteinaceous | Ratings After Process | | Ratings After Three Shampoos | |
|---|---|---|---|---|
| Material | Curl | Color | Curl | Color |
| HYDROTRITICUM 2000 | G | F | G | F |
| CROQUAT M | G | F | G | F |
| HYDROSOY 2000/SF | G | F | G | F |
| CROSILQUAT | G | F | G | F |
| CROTEIN WKP & CROQUAT WKP | E | E | E | E |

Hair processed using the preferred first and second compositions (the control; last row of Table 6) rated excellent in curl and color after the process was completed and after shampooing the hair three times. Substitution of the other proteinaceous materials for the preferred CROTEIN WKP and CROQUAT WKP in the second composition significantly reduced the curl and color of the hair. However, comparison of the Table 6 results with the Table 3 results indicates that for the non-preferred second compositions (the first four rows of each of the two tables), use of the sealer ameliorated the reduction in curl ratings caused by the substitution of other proteinaceous material for the preferred proteinaceous material but generally had no effect on color ratings.

In a seventh set of experiments, the preferred process was run with the preferred second composition but with substitution of various proteinaceous materials in the first composition for the preferred mixture of 0.4% CROTEIN WKP and 0.3% CROQUAT WKP and with sealer (1.5% hydrogen peroxide solution), giving the results noted in Table 7. Thus, the runs reported in Table 7 were essentially the same as the runs reported in Table 4 except for the addition of the sealer.

TABLE 7

| Comp. 1 Proteinaceous | Ratings After Process | | Ratings After Three Shampoos | |
|---|---|---|---|---|
| Material | Curl | Color | Curl | Color |
| HYDROTRITICUM 2000 | G/VG | G | F/G | F/G |
| CROQUAT M | G/VG | G | F/G | F/G |
| HYDROSOY 2000/SF | G/VG | G | F/G | F/G |
| CROSILQUAT | G/VG | G | F/G | F/G |
| CROTEIN WKP & CROQUAT WKP | E | E | E | E |

Hair processed using the preferred first and second compositions rated excellent in both curl and color after the process was completed as well as after shampooing the hair three times (the control; last row of Table 7). Substitution of the other proteinaceous materials for the preferred CROTEIN WKP and CROQUAT WKP in the first composition significantly reduced the curl and color, particularly after the hair was shampooed three times. Comparison of the Table 7 results with the Table 4 results indicates that for the non-preferred first compositions (the first four rows of each of the two tables), use of the sealer ameliorated the reduction in ratings caused by the substitution of other proteinaceous material for the preferred proteinaceous material, particularly in curl rating immediately after the process was complete.

In summary, as compared to hair waved by a conventional process and then colored more than a week later, the hair resulting from the process of this invention has improved shape retention (whether a curled or straightened shape), color receptivity, color stability, color retention (color permanence), color evenness, color depth (intensity), shine, strength, softness, luster, and elasticity. The hair can be shampooed immediately after the process has been completed without substantial damage to curl or color and the curl and color remain excellent even after further shampooing (see, e.g., Tables 2–7, last row).

Obtaining hair that is softer than that obtained with a conventional treatment yet is stronger and has better shape retention is unexpected because increased strength and better shape retention in permanent waved hair are generally associated with a harder, stiffer hair fiber.

As will be understood by one skilled in the art, many variations and modifications may be made and the claims are intended to cover all variations and modifications falling within the true spirit and scope of the invention.

I claim:

1. A process for waving and coloring hair in the same day that can provide to the hair improved shape retention, color receptivity, color stability, color retention, color evenness, color depth, shine, strength, softness, luster, and/or elasticity, the hair containing keratin having disulfide bonds, said process comprising the steps:

(a) optionally shampooing the hair;
(b) contacting the hair with a reducing agent to reduce a sufficient number of the disulfide bonds in the hair to relax the hair to the required degree;

(c) optionally removing excess reducing agent from the reduced hair;
(d) contacting the reduced hair with a first composition containing:
   (i) one or more first biologically acceptable metals; and
   (ii) optionally one or more first proteinaceous materials;
(e) optionally removing excess first composition from the reduced hair;
(f) optionally contacting the reduced hair with a second composition containing:
   (i) one or more second biologically acceptable metals; and
   (ii) optionally one or more second proteinaceous materials;
(g) drying the reduced hair while at least some of the first composition and/or optional second composition is still in contact with the reduced hair so that substantially all of the reduced hair is substantially dry;
(h) contacting the substantially dry reduced hair with an oxidative coloring agent and an oxidizing agent to color the hair and reform a substantial portion of the disulfide bonds in the hair that were reduced in step (b);
(i) optionally contacting the hair with additional oxidizing agent; and
(j) optionally shampooing the hair.

2. The process of claim 1 wherein the hair is on the head of a person.

3. The process of claim 1 wherein at least one of the first and second biologically acceptable metals comprises a polyvalent metal.

4. The process of claim 3 wherein the polyvalent metal is selected from the group consisting of alkaline earth metals, zinc, and aluminum.

5. The process of claim 1 wherein the first and second biologically acceptable metals comprise the same metal.

6. The process of claim 5 wherein the same metal is magnesium.

7. The process of claim 1 wherein at least one of the first and second proteinaceous materials comprises cystine-containing proteinaceous materials that can form disulfide bonds involving the keratin of the hair.

8. The process of claim 7 wherein at least some of the cystine-containing proteinaceous materials have an average molecular weight of about 5,000 or less.

9. The process of claim 8 wherein at least some of the cystine-containing proteinaceous materials have a cystine content of at least about 5%.

10. The process of claim 9 wherein the cystine-containing proteinaceous materials comprise non-ionic and cationic cystine-containing proteinaceous materials.

11. The process of claim 1 wherein in the first composition at least one of the first biologically acceptable metals comprises a polyvalent metal and at least one of the first proteinaceous materials is present and it comprises one or more cystine-containing proteinaceous materials that can form disulfide bonds involving the keratin of the hair, and wherein the pH of the first composition is from about 2 to about 4.

12. The process of claim 11 wherein in the first composition the polyvalent metal is magnesium and the cystine-containing proteinaceous materials together have an average molecular weight of about 5,000 or less and an average cystine content of at least about 5%.

13. The process of claim 11 wherein the concentration of the cystine in the first composition is at least about 0.005% by weight.

14. The process of claim 1 wherein the second composition is contacted with the reduced hair and in the second composition at least one of the second biologically acceptable metals comprises a polyvalent metal and at least one of the second proteinaceous materials is present and it comprises one or more cystine-containing proteinaceous materials that can form disulfide bonds involving the keratin of the hair, and wherein the pH of the second composition is from about 2 to about 4.

15. The process of claim 14 wherein in the second composition the polyvalent metal is magnesium and the cystine-containing proteinaceous materials together have an average molecular weight of about 5,000 or less and an average cystine content of at least about 5%.

16. The process of claim 14 wherein the concentration of the cystine in the second composition is at least about 0.005% by weight.

17. The process of any of the preceding claims wherein there is no rinsing of the hair from step (b) through step (g) so that drying step (g) comprises drying the hair while at least some of the reducing agent and at least some of the first composition and/or optional second composition are still in contact with the hair so that substantially all of the hair is substantially dry.

18. The process of any of claims 1 to 16 wherein the hair is placed on forming members prior to step (b) and the hair is not removed from the forming members until after step (h).

19. The process of claim 18 wherein there is no rinsing of the hair from step (b) through step (g) so that drying step (g) comprises drying the hair while at least some of the reducing agent and at least some of the first composition and/or optional second composition are still in contact with the hair so that substantially all of the hair is substantially dry.

20. A process for waving and coloring hair on the head of a person in the same day that can provide to the hair improved shape retention, color receptivity, color stability, color retention, color evenness, color depth, shine, strength, softness, luster, and/or elasticity, the hair containing keratin having disulfide bonds, said process comprising the steps:
   (a) optionally shampooing the hair;
   (b) placing the hair on one or more forming members;
   (c) contacting the hair while it is on the one or more forming members with a reducing agent to reduce a sufficient number of the disulfide bonds in the hair to relax the hair to the required degree;
   (d) optionally removing excess reducing agent from the reduced hair;
   (e) contacting the reduced hair while it is on the one or more forming members with a first composition having a pH of less than about 7 and containing:
      (i) at least 0.05% by weight total of one or more first biologically acceptable metals; and
      (ii) at least 0.01% by weight total of one or more first cystine-containing proteinaceous materials that can form disulfide bonds involving the keratin of the hair;
   (f) optionally removing excess first composition from the reduced hair while it is on the one or more forming members;
   (g) contacting the reduced hair while it is on the one or more forming members with a second composition having a pH of less than about 7 and containing:
      (i) at least 0.05% by weight total of one or more second biologically acceptable metals; and
      (ii) at least 0.01% by weight total of one or more second cystine-containing proteinaceous materials that can form disulfide bonds involving the keratin of the hair;

(h) drying the reduced hair while it is on the one or more forming members and while at least some of the first composition and/or second composition is still in contact with the reduced hair so that substantially all of the reduced hair is substantially dry;

(i) contacting the substantially dry reduced hair while it is on the one or more forming members with an oxidative coloring agent and an oxidizing agent to color the hair and reform a substantial portion of the disulfide bonds in the hair that were reduced in step (c);

(j) optionally contacting the hair while it is on the one or more forming members with additional oxidizing agent;

(k) removing the hair from the one or more forming members; and (l) optionally shampooing the hair.

21. The process of claim 20 wherein at least one of the first and second biologically acceptable metals comprises a polyvalent metal.

22. The process of claim 21 wherein the polyvalent metal is selected from the group consisting of alkaline earth metals, zinc, and aluminum.

23. The process of claim 20 wherein the first and second biologically acceptable metals comprise the same metal.

24. The process of claim 23 wherein the same metal is magnesium.

25. The process of claim 20 wherein the first cystine-containing proteinaceous materials together have an average molecular weight of about 5,000 or less and the second cystine-containing proteinaceous materials together have an average molecular weight of about 5,000 or less.

26. The process of claim 25 wherein the first cystine-containing proteinaceous materials together have an average cystine content of at least about 1% and the second cystine-containing proteinaceous materials together have an average cystine content of at least about 1%.

27. The process of claim 26 wherein the first cystine-containing proteinaceous materials comprise non-ionic and cationic cystine-containing proteinaceous materials and the second cystine-containing proteinaceous materials comprise non-ionic and cationic cystine-containing proteinaceous materials.

28. The process of claim 20 wherein the concentration of the cystine in each of the first composition and second composition is at least about 0.005% by weight.

29. The process of any of claims 20 to 28 wherein there is no rinsing of the hair from step (c) through step (h) so that drying step (h) comprises drying the hair while at least some of the reducing agent, first composition, and second composition are still in contact with the hair so that substantially all of the hair is substantially dry.

30. A process for waving and coloring hair on the head of a person in the same day that can provide to the hair improved shape retention, color receptivity, color stability, color retention, color evenness, color depth, shine, strength, softness, luster, and/or elasticity, the hair containing keratin having disulfide bonds, said process comprising the steps:

(a) optionally shampooing the hair;

(b) placing the hair on one or more forming members;

(c) contacting the hair while it is on the one or more forming members with a reducing agent to reduce a sufficient number of the disulfide bonds in the hair to relax the hair to the required degree;

(d) optionally removing excess reducing agent from the reduced hair;

(e) contacting the reduced hair while it is on the one or more forming members with a first composition having a pH of from about 1 to about 6 and containing:

(i) at least 0.05% by weight total of one or more first biologically acceptable polyvalent metals selected from the group consisting of alkaline earth metals, zinc, and aluminum; and (ii) at least 0.01% by weight total of one or more first cystine-containing proteinaceous materials that can form disulfide bonds involving the keratin of the hair, that together have an average molecular weight of about 5,000 or less, and that together have an average cystine content of at least about 1%, the concentration of the cystine in the first composition being at least about 0.005% by weight;

(f) optionally removing excess first composition from the reduced hair while it is on the one or more forming members;

(g) contacting the reduced hair while it is on the one or more forming members with a second composition having a pH of from about 1 to about 6 and containing:

(i) at least 0.05% by weight total of one or more second biologically acceptable polyvalent metals selected from the group consisting of alkaline earth metals, zinc, and aluminum; and (ii) at least 0.01% by weight total of one or more second cystine-containing proteinaceous materials that can form disulfide bonds involving the keratin of the hair, that together have an average molecular weight of about 5,000 or less, and that together have an average cystine content of at least about 1%, the concentration of the cystine in the first composition being at least about 0.005% by weight;

(h) drying the reduced hair while it is on the one or more forming members and while at least some of the first composition and/or second composition is still in contact with the reduced hair so that substantially all of the reduced hair is substantially dry;

(i) contacting the substantially dry reduced hair while it is on the one or more forming members with an oxidative coloring agent and an oxidizing agent to color the hair and reform a substantial portion of the disulfide bonds in the hair that were reduced in step (c);

(j) optionally contacting the hair while it is on the one or more forming members with additional oxidizing agent;

(k) removing the hair from the one or more forming members; and (l) optionally shampooing the hair.

31. The process of claim 30 wherein the first and second biologically acceptable metals comprise the same metal.

32. The process of claim 31 wherein the same metal is magnesium.

33. The process of claim 30 wherein the first cystine-containing proteinaceous materials comprise non-ionic and cationic cystine-containing proteinaceous materials and the second cystine-containing proteinaceous materials comprise non-ionic and cationic cystine-containing proteinaceous materials.

34. The process of claim 30 wherein the concentration of the cystine in the first composition is at least about 0.01% by weight.

35. The process of claim 30 wherein the concentration of the cystine in the second composition is at least about 0.01% by weight.

36. The process of any of claims 30 to 35 wherein there is no rinsing of the hair from step (c) through step (h) so that drying step (h) comprises drying the hair while at least some of the reducing agent, first composition, and second composition are still in contact with the hair so that substantially all of the hair is substantially dry.

37. A process for waving and coloring hair on the head of a person in a period of not more than about six hours that can provide to the hair improved shape retention, color receptivity, color stability, color retention, color evenness, color depth, shine, strength, softness, luster, and/or elasticity, the hair containing keratin having disulfide bonds, said process comprising the steps:

(a) optionally shampooing the hair;

(b) placing the hair on one or more forming members;

(c) contacting the hair while it is on the one or more forming members with a reducing agent to reduce a portion of the disulfide bonds in the hair, thereby producing reduced hair that is sufficiently reduced so that the hair will remain in the desired configuration after step (l);

(d) optionally removing excess reducing agent from the reduced hair;

(e) contacting the reduced hair while it is on the one or more forming members with a first composition having a pH of from about 1 to about 6 and containing:

(i) at least 0.05% by weight total of one or more first biologically acceptable polyvalent metals selected from the group consisting of alkaline earth metals, zinc, and aluminum; and (ii) at least 0.01% by weight total of one or more first cystine-containing proteinaceous materials that can form disulfide bonds involving the keratin of the hair, that together have an average molecular weight of about 5,000 or less, and that together have an average cystine content of at least about 1%, the concentration of the cystine in the first composition being at least about 0.01% by weight;

(f) optionally removing excess first composition from the reduced hair while it is on the one or more forming members;

(g) contacting the reduced hair while it is on the one or more forming members with a second composition having a pH of from about 1 to about 6 and containing:

(i) at least 0.05% by weight total of one or more second biologically acceptable polyvalent metals selected from the group consisting of alkaline earth metals, zinc, and aluminum; and (ii) at least 0.01% by weight total of one or more second cystine-containing proteinaceous materials that can form disulfide bonds involving the keratin of the hair, that together have an average molecular weight of about 5,000 or less, and that together have an average cystine content of at least about 1%, the concentration of the cystine in the first composition being at least about 0.01% by weight;

(h) drying the reduced hair while it is on the one or more forming members and while at least some of the first composition and/or second composition is still in contact with the reduced hair so that substantially all of the reduced hair is substantially dry;

(i) contacting the substantially dry reduced and relaxed hair while it is on the one or more forming members with an oxidative coloring agent and an oxidizing agent to color the hair and reform a substantial portion of the disulfide bonds in the hair that were reduced in step (c);

(j) optionally contacting the hair from step (i) while it is on the one or more forming members with additional oxidizing agent;

(k) removing the hair from the one or more forming members; and (l) optionally shampooing the hair.

38. The process of claim 37 wherein the concentration of the cystine in the first composition is at least about 0.015% by weight.

39. The process of claim 37 wherein the concentration of the cystine in the second composition is at least about 0.03% by weight.

40. The process of any of claims 37 to 39 wherein there is no rinsing of the hair from step (c) through step (h) so that drying step (h) comprises drying the hair while at least some of the reducing agent, first composition, and second composition are still in contact with the hair so that substantially all of the hair is substantially dry.

41. The process of claim 40 wherein in step (e) substantially all of the scalp is contacted with the first composition and in step (g) substantially all of the scalp is contacted with the second composition.

42. The process of claim 41 wherein the pH of the first composition is from about 2 to about 3.5 and the pH of the second composition is from about 3.3 to about 4.3.

* * * * *